(12) United States Patent
Skiba et al.

(10) Patent No.: US 6,482,210 B1
(45) Date of Patent: Nov. 19, 2002

(54) SOFT TISSUE/LIGAMENT TO BONE FIXATION DEVICE WITH INSERTER

(75) Inventors: Jeffry B. Skiba, Santa Rosa, CA (US); Jeffrey P. Baldwin, Phoenix, AZ (US)

(73) Assignee: Orthopaedic Biosystems, Ltd., Inc., Scottsdale, AZ (US)

( * ) Notice: Subject to any disclaimer, the term of this patent is extended or adjusted under 35 U.S.C. 154(b) by 0 days.

(21) Appl. No.: 09/439,143

(22) Filed: Nov. 12, 1999

Related U.S. Application Data

(60) Provisional application No. 60/108,087, filed on Nov. 12, 1998.

(51) Int. Cl.[7] .................................................. A61F 5/00
(52) U.S. Cl. ........................ 606/86; 606/88; 623/13.11
(58) Field of Search ............................... 606/69, 65, 71, 606/72, 73, 75, 76, 86, 88, 89, 139, 232; 623/13.11, 13.12, 13.14

(56) References Cited

U.S. PATENT DOCUMENTS

| | | |
|---|---|---|
| 1,247,621 A | 11/1917 | Bennett |
| 2,100,570 A | 11/1937 | Saleh |
| 2,143,086 A | 1/1939 | Pleister |
| 2,213,715 A | 9/1940 | Monahan |
| 2,453,056 A | 11/1948 | Zack |
| 2,562,419 A | 7/1951 | Ferris |
| 2,665,597 A | 1/1954 | Hill |
| 3,033,155 A | 5/1962 | Mielzynski et al. |
| 3,103,666 A | 9/1963 | Bone |
| 3,143,915 A | 8/1964 | Tendler |
| 3,227,031 A | 1/1966 | Williams |
| 3,316,796 A | 5/1967 | Young |
| 3,399,432 A | 9/1968 | Merser |
| 3,470,834 A | 10/1969 | Bone |
| 3,638,653 A | 2/1972 | Berry |
| 3,664,345 A | 5/1972 | Dabbs et al. |
| 3,699,969 A | 10/1972 | Allen |
| 3,875,648 A | 4/1975 | Bone |
| 3,894,467 A | 7/1975 | Brescia |
| 3,931,667 A | 1/1976 | Merser et al. |
| 3,976,079 A | 8/1976 | Samuels et al. |
| 3,990,619 A | 11/1976 | Russell |
| 4,013,071 A | 3/1977 | Rosenberg |
| 4,275,717 A | 6/1981 | Bolesky |
| 4,287,807 A | 9/1981 | Pacharis et al. |
| 4,293,259 A | 10/1981 | Liebig |

(List continued on next page.)

FOREIGN PATENT DOCUMENTS

| | | |
|---|---|---|
| EP | 0615732 A1 | 9/1994 |
| EP | 0674880 A1 | 10/1995 |
| FR | 1368021 | 6/1964 |
| FR | 2622430 | 5/1989 |
| GB | 343992 | 3/1931 |
| WO | WO 86/03666 | 7/1986 |
| WO | WO 87/01270 | 3/1987 |
| WO | WO 89/10096 | 11/1989 |
| WO | WO 92/04874 | 4/1992 |
| WO | WO 95/25469 | 9/1995 |
| WO | WO 95/27449 | 10/1995 |

OTHER PUBLICATIONS

ROC™ Fastener System, Innovative Devices, Inc., 1994.

*Primary Examiner*—Pedro Philogene
(74) *Attorney, Agent, or Firm*—Fish & Richardson P.C.

(57) ABSTRACT

A system of instrumentation and implants for surgically securing an allograft or prosthetic ligament into a patient's bone is part of a procedure to replace cruciate ligaments. A fixation device for attaching soft tissue to bone includes a fixation mechanism, a shaft, and a securing mechanism. Alternatively, the fixation mechanism may include an expansion leg, the shaft may include a one-way track. In another implementation, the fixation mechanism may include an inner core that expands as a result of insertion of a device that causes radial displacement.

4 Claims, 9 Drawing Sheets

U.S. PATENT DOCUMENTS

| | | | |
|---|---|---|---|
| 4,386,515 A | 6/1983 | Starke | |
| 4,409,974 A | 10/1983 | Freedland | |
| 4,447,915 A | 5/1984 | Weber | |
| 4,525,114 A | 6/1985 | Hirst | |
| 4,532,926 A | 8/1985 | O'Holla | |
| 4,573,844 A | 3/1986 | Smith | |
| 4,590,928 A | 5/1986 | Hunt et al. | |
| 4,605,414 A | 8/1986 | Czajka | |
| 4,636,121 A | 1/1987 | Miller | |
| 4,669,473 A | 6/1987 | Richards et al. | |
| 4,708,132 A | 11/1987 | Silverstrini | |
| 4,711,234 A | 12/1987 | Vives et al. | |
| 4,738,255 A | 4/1988 | Goble et al. | |
| 4,741,330 A | 5/1988 | Hayhurst | |
| 4,744,353 A | 5/1988 | McFarland | |
| 4,744,793 A | 5/1988 | Parr et al. | |
| 4,772,286 A | 9/1988 | Goble et al. | |
| 4,776,328 A | 10/1988 | Frey et al. | |
| 4,776,330 A | 10/1988 | Chapman et al. | |
| 4,793,335 A | 12/1988 | Frey et al. | |
| 4,870,957 A | 10/1989 | Goble et al. | |
| 4,898,156 A | 2/1990 | Gatturna et al. | |
| 4,899,743 A | 2/1990 | Nicholson et al. | |
| 4,927,421 A | 5/1990 | Goble et al. | |
| 4,946,468 A | 8/1990 | Li | |
| 4,968,315 A | 11/1990 | Gatturna | |
| 4,988,351 A | 1/1991 | Paulos et al. | |
| 4,997,433 A | 3/1991 | Goble et al. | |
| 5,002,550 A | 3/1991 | Li | |
| 5,002,574 A | 3/1991 | May et al. | |
| 5,013,316 A | 5/1991 | Goble et al. | |
| 5,037,422 A | 8/1991 | Hayhurst et al. | |
| 5,041,129 A | 8/1991 | Hayhurst et al. | |
| 5,046,513 A | 9/1991 | Gatturna et al. | |
| 5,092,891 A | 3/1992 | Kummer et al. | |
| 5,094,563 A | 3/1992 | Carletti | |
| 5,100,417 A | 3/1992 | Cerier et al. | |
| 5,102,421 A | 4/1992 | Anspach, Jr. | |
| 5,129,902 A | 7/1992 | Goble et al. | |
| 5,139,520 A | 8/1992 | Rosenberg | |
| 5,141,520 A | 8/1992 | Goble et al. | |
| 5,147,166 A | 9/1992 | Harker | |
| 5,147,362 A | 9/1992 | Goble | |
| 5,152,790 A | 10/1992 | Rosenberg et al. | |
| 5,161,916 A | 11/1992 | White et al. | |
| D331,626 S | 12/1992 | Hayhurst et al. | |
| 5,167,665 A | 12/1992 | McKinney | |
| 5,176,682 A | 1/1993 | Chow | |
| 5,192,303 A | 3/1993 | Gatturna et al. | |
| 5,203,787 A | 4/1993 | Noblitt et al. | |
| 5,207,679 A | 5/1993 | Li | |
| 5,209,753 A | 5/1993 | Biedermann et al. | |
| 5,211,647 A | 5/1993 | Schmeiding | |
| RE34,293 E | 6/1993 | Goble et al. | |
| 5,217,486 A | 6/1993 | Rice et al. | |
| 5,224,946 A | 7/1993 | Hayhurst et al. | |
| 5,236,445 A | 8/1993 | Hayhurst et al. | |
| 5,258,016 A | 11/1993 | DiPoto et al. | |
| 5,263,802 A | 11/1993 | Fichot et al. | |
| 5,268,001 A | 12/1993 | Nicholson et al. | |
| 5,269,809 A | 12/1993 | Hayhurst et al. | |
| 5,306,290 A | 4/1994 | Martins et al. | |
| 5,312,438 A | 5/1994 | Johnson | |
| 5,324,308 A | 6/1994 | Pierce | |
| 5,326,205 A | 7/1994 | Anspach, Jr. et al. | |
| 5,336,225 A | 8/1994 | Zang | |
| 5,350,380 A | 9/1994 | Goble et al. | |
| 5,354,298 A | 10/1994 | Lee et al. | |
| 5,356,413 A | * 10/1994 | Martins et al. | 606/75 |
| 5,358,511 A | 10/1994 | Gatturna et al. | |
| 5,364,400 A | 11/1994 | Rego, Jr. et al. | |
| 5,372,599 A | 12/1994 | Martins | |
| 5,372,604 A | 12/1994 | Trott | |
| 5,374,269 A | * 12/1994 | Rosenberg | 606/86 |
| 5,376,120 A | 12/1994 | Sarver et al. | |
| 5,383,878 A | 1/1995 | Roger et al. | |
| 5,393,302 A | 2/1995 | Clark et al. | |
| 5,397,356 A | 3/1995 | Goble et al. | |
| 5,411,523 A | 5/1995 | Goble | |
| 5,417,691 A | 5/1995 | Hayhurst | |
| 5,417,712 A | 5/1995 | Whittaker et al. | |
| 5,423,819 A | 6/1995 | Small et al. | |
| 5,425,733 A | 6/1995 | Schmieding | |
| 5,425,767 A | 6/1995 | Steininger et al. | |
| 5,431,651 A | 7/1995 | Goble | |
| 5,439,684 A | 8/1995 | Prewett et al. | |
| 5,441,502 A | 8/1995 | Bartlett | |
| 5,443,482 A | 8/1995 | Stone et al. | |
| 5,443,509 A | 8/1995 | Boucher et al. | |
| 5,454,811 A | 10/1995 | Huebner | |
| 5,456,685 A | 10/1995 | Huebner | |
| 5,458,601 A | 10/1995 | Young, Jr. et al. | |
| 5,464,425 A | 11/1995 | Skiba | |
| 5,464,427 A | 11/1995 | Curtis et al. | |
| 5,470,334 A | 11/1995 | Ross et al. | |
| 5,480,403 A | 1/1996 | Lee et al. | |
| 5,486,197 A | 1/1996 | Le et al. | |
| 5,500,001 A | 3/1996 | Trott | |
| 5,501,683 A | 3/1996 | Trott | |
| 5,501,695 A | 3/1996 | Anspach, Jr. et al. | |
| 5,505,735 A | 4/1996 | Li | |
| 5,520,691 A | 5/1996 | Branch | |
| 5,522,843 A | 6/1996 | Zang | |
| 5,522,845 A | 6/1996 | Wenstrom, Jr. | |
| 5,531,792 A | 7/1996 | Huene | |
| 5,534,004 A | 7/1996 | Santangelo | |
| 5,545,180 A | 8/1996 | Le et al. | |
| 5,554,171 A | 9/1996 | Gatturna et al. | |
| 5,562,669 A | * 10/1996 | McGuire | 606/72 |
| 5,571,104 A | 11/1996 | Li | |
| 5,573,548 A | 11/1996 | Nazre et al. | |
| 5,584,835 A | 12/1996 | Greenfield | |
| 5,584,860 A | 12/1996 | Goble et al. | |
| 5,601,557 A | 2/1997 | Hayhurst | |
| 5,632,748 A | * 5/1997 | Beck, Jr. et al. | 606/89 |
| 5,643,266 A | 7/1997 | Li | |
| 5,643,321 A | 7/1997 | McDevitt | |
| 5,645,589 A | 7/1997 | Li | |
| 5,647,874 A | 7/1997 | Hayhurst | |
| 5,649,963 A | 7/1997 | McDevitt | |
| 5,662,654 A | 9/1997 | Thompson | |
| 5,667,510 A | * 9/1997 | Combs | 606/86 |
| 5,674,224 A | * 10/1997 | Howell et al. | 606/88 |
| 5,683,418 A | 11/1997 | Luscombe et al. | |
| 5,690,649 A | 11/1997 | Li | |
| 5,690,676 A | 11/1997 | DiPoto et al. | |
| 5,707,395 A | 1/1998 | Li | |
| 5,720,766 A | 2/1998 | Zang et al. | |
| 5,743,914 A | 4/1998 | Skiba | |
| 5,785,714 A | * 7/1998 | Morgan et al. | 606/86 |
| 5,899,938 A | 5/1999 | Sklar et al. | |
| 6,086,591 A | 7/2000 | Bojarski | |
| 6,117,139 A | * 9/2000 | Shino | 606/86 |
| 6,146,406 A | 11/2000 | Shluzas et al. | |

\* cited by examiner

SOFT TISSUE/LIGAMENT TO BONE FIXATION DEVICE WITH INSERTER

This application claims the benefit of prior provisional application, Provisional Application Ser. No. 60/108,087, filed Nov. 12, 1998.

TECHNICAL FIELD

This invention relates to surgical reattachment of soft tissue/ligament to bone, and more particularly, instrumentation for surgically securing an allograft or prosthetic ligament into a patient's bone as part of a procedure to replace cruciate ligaments.

BACKGROUND

Surgical re-attachment of soft tissue to bone due to traumatic injury or surgical procedures has created a need for efficient and time-saving instruments, implants, and procedures. Current methods of re-attachment of soft tissue to bone include bone tunnels, surgical staples, surgical tacks, interference screws, and bone anchors. If the desired result is solely approximation of the soft tissue back to the bony insertion site, the aforementioned devices can be used within certain limitations. There are, however, certain tendons and ligaments, which present the surgeon with a very specific set of constraints, for example, grafting of a tendon into the site of an irreparably torn anterior cruciate ligament in the human knee.

Each repair technique has a unique set of constraints. For instance, interference screws are difficult to insert and can damage a graft on insertion. In order to insert an interference screw, a large hole must be drilled to accommodate the graft and the screw. The screw prevents bone to tendon fixation around the screw, can leave a weak defect in the bone, and can vascularize the area under compression. In another instance, bone tunnels require additional incisions and trauma to the patient. With a bone tunnel, there is little radial compression on the graft to the bone site and the securing suture may creep or be cut by the bone, and the securing knot may slip. With surgical staples, again additional incisions and trauma to the patient occurs, and there is little radial compression on the graft to the bone site. The surgical staple may even not stay in the bone. In another example, using a device having an internal screw in a tunnel and a ratcheting inner element that presses into the outer screw in anterior cruciate ligament (ACL) repair does not provide radial compression for graft healing. Also, such a device is difficult to revise.

SUMMARY

A system of instrumentation and implants for surgically securing an allograft or prosthetic ligament into a patient's bone is used in a procedure to replace a patient's cruciate ligaments. In one general aspect, a device for attaching soft tissue to bone includes a fixation mechanism, a shaft, and a securing mechanism, which slides along the shaft. The securing mechanism may include an internal one-way locking mechanism.

In another aspect, a device for attaching soft tissue to bone includes a shaft, a fixation mechanism attached to the shaft, a one-way track for inserting the shaft therein and the fixation mechanism therethrough; and a securing mechanism for holding a graft within the one-way track by compressing the securing mechanism against the graft. The securing mechanism may be at least one of a conical shape, a cylindrical shape, a cubic shape, or a complex shape capable of exerting an adequate radial force against the graft and into a surrounding bone. The fixation device may include a fixation mechanism with an expansion leg, a shaft with a one-way track, and a securing mechanism. The expansion leg of the fixation mechanism may be single or multiple legs or may be toggles, legs, expansion arms, barbs, tines, or other apparatuses to prevent backward translation. The one-way track of the shaft may be a single length or multiple lengths, i.e., an adjustable length member. The securing mechanism holds the tissue and has an internal one-way lock, which slides along the one-way track. Alternatively, the fixation mechanism may include an inner core that expands as a result of the insertion of a device that causes radial displacement, for example, a wedge, a tapered plug, or a screw.

A fixation device may be made of any biocompatible metal, such as titanium or stainless steel, plastic, such as nylon or polyester, or bioabsorbable, such as PLLA. Any material suitable for use in the body can be used. The material must provide adequate resistance to creep, hold the load required, and not be affected by cyclic loading.

The details of one or more implementations are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION

Figure 1:
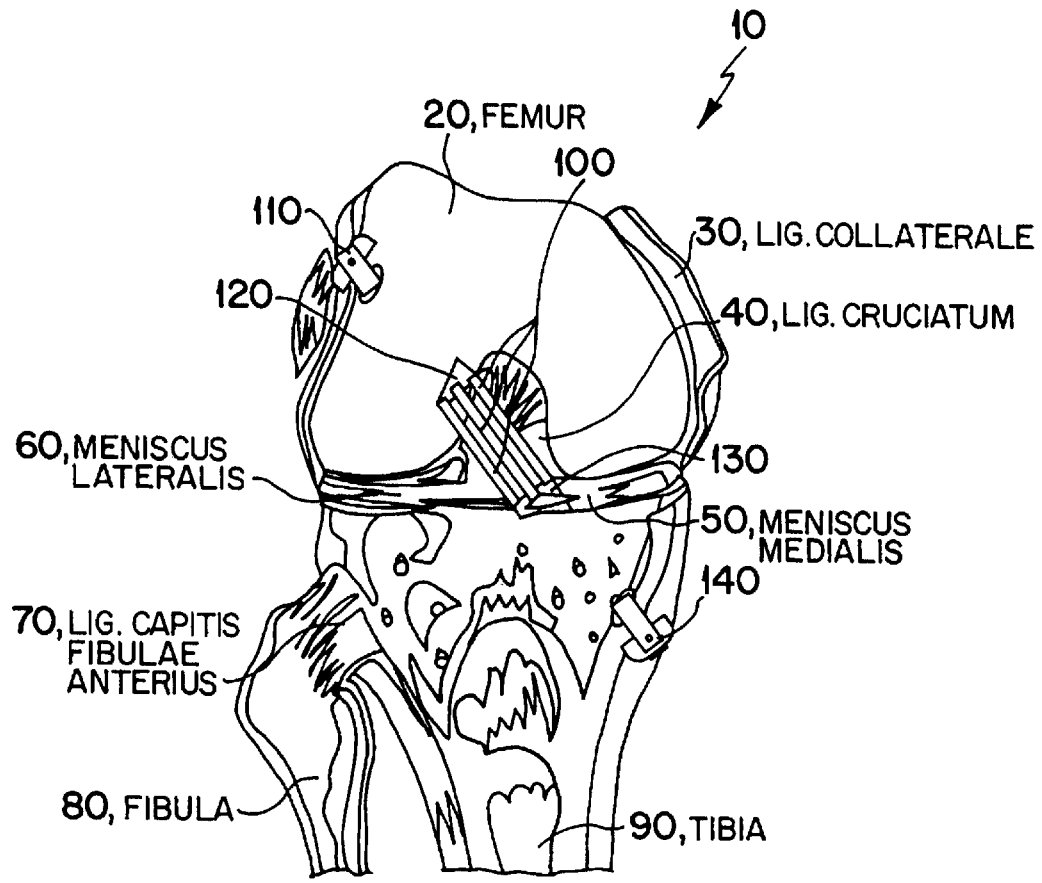
FIG. 1 is a representation of a human knee with an ACL graft held in place, generally in accordance with the fixation device.

FIG. 1 is a representation of a human knee with an ACL graft 100 (three lines) held in place the joint space between the tibia 90 and the femur 20 by a fixation device. The fixation device includes two fixation mechanisms 110, 140 and two securing mechanisms 120, 130. Each fixation mechanism 110, 140 has a locking strip (not shown) and is connected to its respective securing mechanism 120, 130 by a one-way locking mechanism (not shown).

Figure 2A:
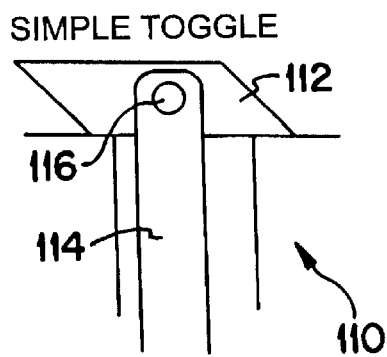
FIGS. 2A–2T are examples of various fixation mechanisms.
Figure 2B:
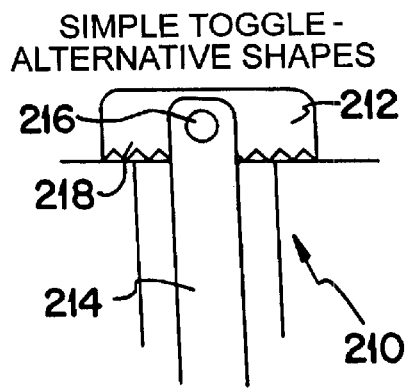
Figure 2C:
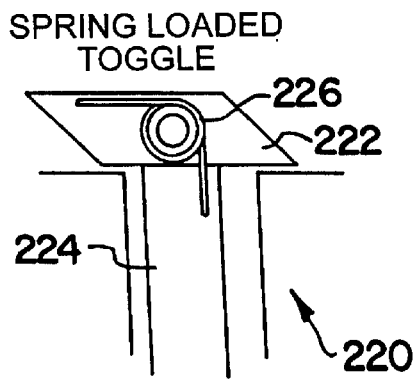
Figure 2D:
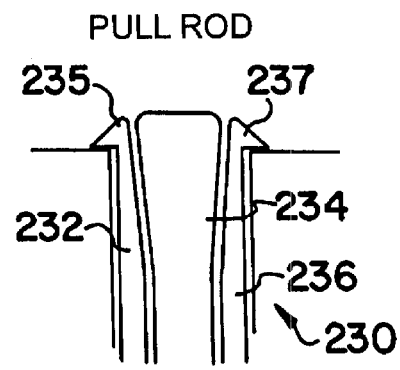
Figure 2E:
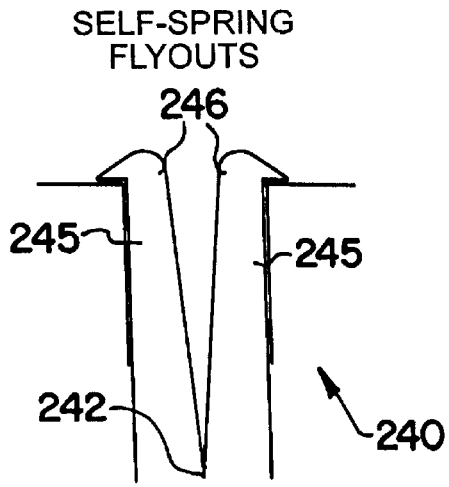
Figure 2F:
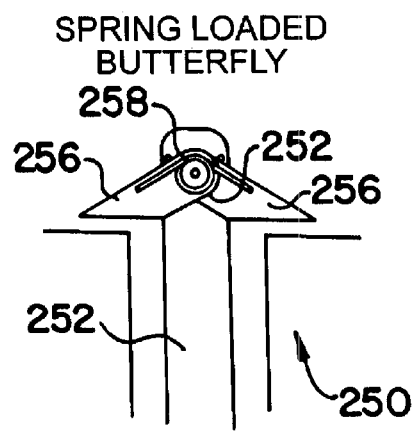
Figure 2G:
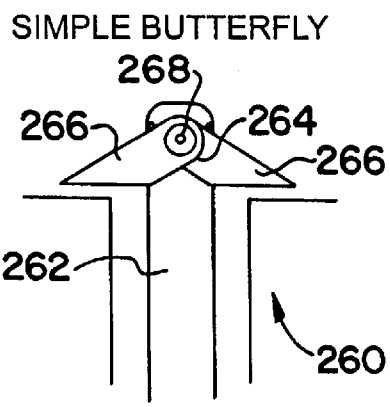
Figure 2H:
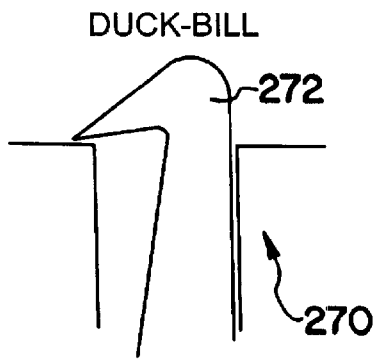
Figure 2I:
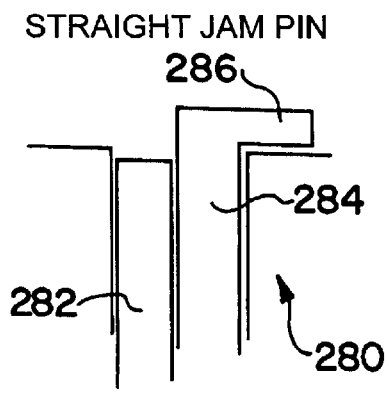
Figure 2J:
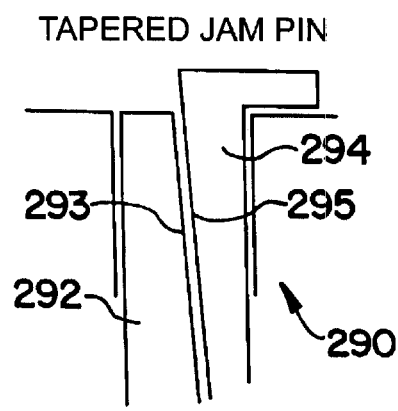
Figure 2K:
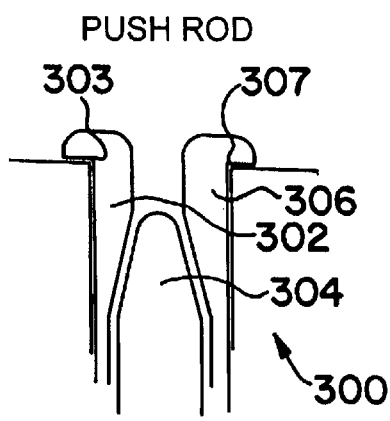
Figure 2L:
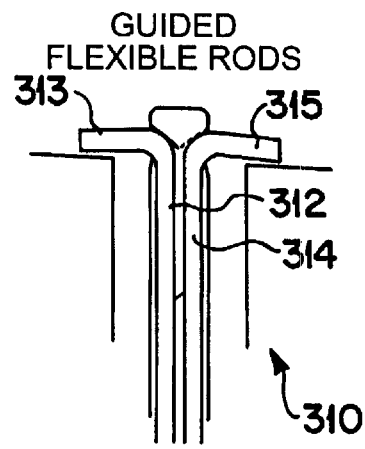
Figure 2M:
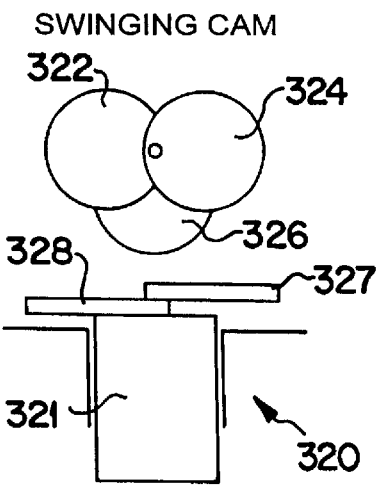
Figure 2N:
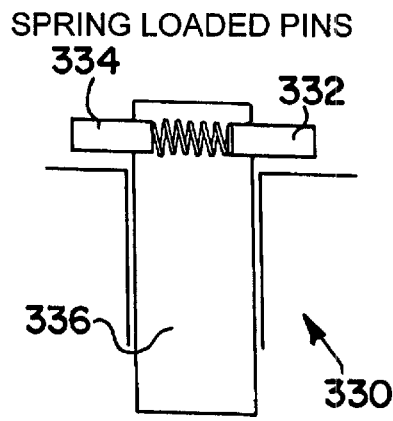
Figure 2O:
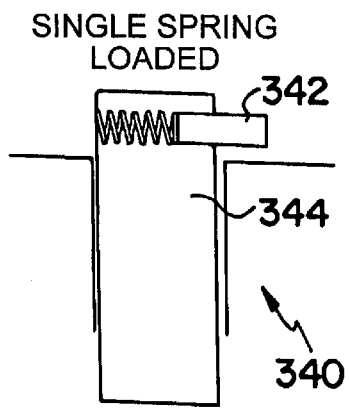
Figure 2P:
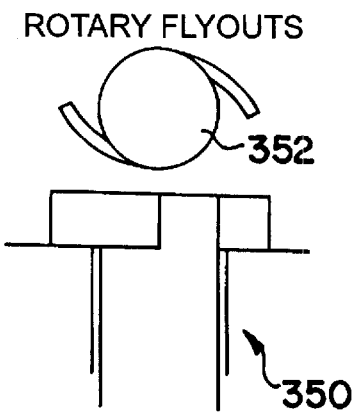
Figure 2Q:
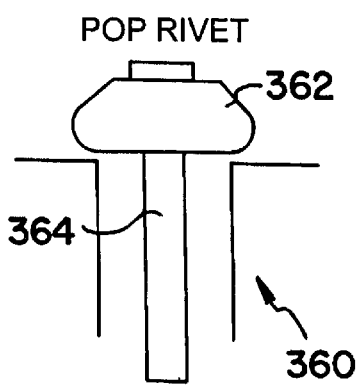
Figure 2R:
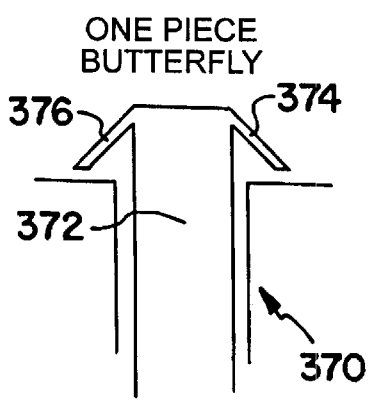
Figure 2S:
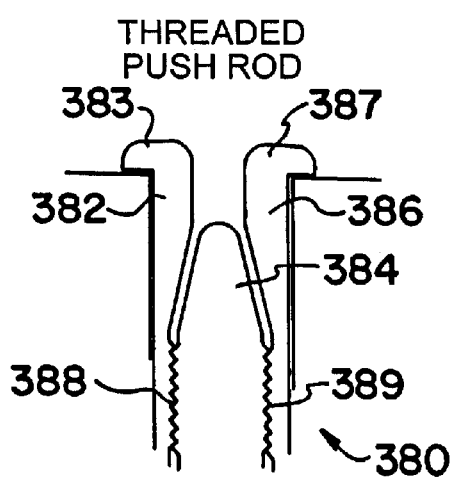
Figure 2T:
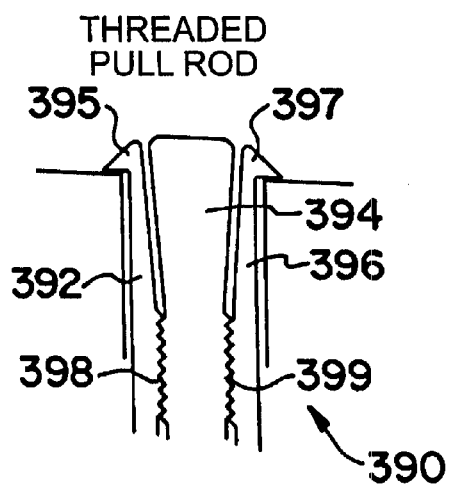

FIGS. 2A–2T are examples of various fixation mechanisms. The fixation mechanism provides resistance to the tensile forces, which are exerted on the graft site. Generally, the length of the fixation mechanism is greater than its width. A fixation mechanism may include a toggle pin member or a toggle element, as shown, for example, in FIGS. 2A–2C. FIG. 2A is a simple toggle fixation mechanism 110 having a parallelogram shaped piece horizontal member 112 (as seen also in FIG. 1) attached to a longitudinal member 114. The longitudinal member 114, which is disposed in the insertion tunnel, may be attached to the horizontal member 112 by a pin or screw or the like 116.

FIG. 2B is an alternative form of a simple toggle fixation mechanism 210 that has a rectangular shaped horizontal member 212 attached to a longitudinal member 214 by a pin or screw or the like 216. The rectangular shaped horizontal member 212 has a plurality of teeth 218 disposed along one side.

FIG. 2C is a spring-loaded toggle fixation mechanism 220 that has a parallelogram-shaped horizontal member 222 attached to a longitudinal member 224 by a spring 226.

FIG. 2D is a pull rod fixation mechanism 230 comprised of three longitudinal members 232, 234, 236. Two of the three longitudinal members 232, 236 have a duck-bill-like head portion 235, 237, which extends over the edge of the insertion tunnel to hold the fixation mechanism in place.

FIG. 2E is a self-spring flyout fixation mechanism 240 comprised of two longitudinal members 245 connected together at their base 242. Each longitudinal member 245 has a duck-bill-like head portion 246, which extends over the edge of the insertion tunnel to hold the fixation mechanism in place.

FIG. 2F is a spring-loaded butterfly fixation mechanism 250 that has a longitudinal member 252 and a butterfly-shaped horizontal member 254 comprised of two arms 256. The arms 256 of the butterfly-shaped horizontal member 254 are connected together and to longitudinal member 252 by a spring 258.

FIG. 2G is a simple butterfly fixation mechanism 260 that has a longitudinal member 262 and a butterfly-shaped horizontal member 264 comprised of two arms 266. The arms 266 of the butterfly-shaped horizontal member 264 are connected together and to the longitudinal member 262 by a pin or screw or the like 268.

FIG. 2H is a duck-bill-shaped fixation mechanism 270. As shown, the head of the fixation mechanism looks like a duck-bill 272 such that the bill portion extends over an edge of the insertion tunnel to hold the fixation mechanism in place.

FIG. 2I is a straight jam pin fixation mechanism 280 comprised of a first longitudinal member 282 and a second longitudinal member 284 with a horizontal portion 286. The horizontal portion 286 extends over an edge of the insertion tunnel to hold the fixation mechanism in place. FIG. 2J is a tapered jam pin fixation mechanism 290 similar to the straight jam pin of FIG. 2I. However, the interior contacting sides 293, 295 of the first longitudinal member 292 and the longitudinal portion of the second longitudinal member 294 are reciprocally tapered.

FIG. 2K is a push rod fixation mechanism 300 comprising three longitudinal members 302, 304, 306. The two outer longitudinal members 302, 306 have respective horizontal portions 303, 307 that extend over the edges of the insertion tunnel to hold the fixation mechanism in place. The interior longitudinal member 304 is shaped like a blunt pen tip. The respective longitudinal portions 308, 309 of the outer longitudinal members 302, 306 are shaped around the blunt pen tip shape of the interior longitudinal member 304.

FIG. 2L is a fixation mechanism 310 formed of guided flexible rods 312, 314. The rods 312, 314 each have a horizontal portion 313, 315, which extend over the edges of the insertion tunnel to hold the fixation mechanism in place.

FIG. 2M is a swinging cam fixation mechanism 320 with three circular members 322, 324, 326, two horizontal members 327, 328, and a block-shaped member 321, which is disposed in the insertion tunnel.

FIG. 2N is a fixation mechanism 330 that includes spring loaded pins 332, 334 disposed on a longitudinal member 336. FIG. 2O is a fixation mechanism 340 that has a single spring-loaded pin 342 disposed on a longitudinal member 344. FIG. 2P is a fixation mechanism 350 that includes rotary flyouts 352.

FIG. 2Q is a fixation mechanism 360 with a pop rivet 362 disposed on the longitudinal member 364. FIG. 2R is a one-piece butterfly 370 having a longitudinal member 372 disposed in the insertion tunnel and two arms 374, 376 that extend over the respective edge of the insertion tunnel.

FIG. 2S is a threaded push rod fixation mechanism 380 similar in shape and form to the push rod fixation mechanism shown in FIG. 2K. However, threaded push rod fixation mechanism 380 has thread portions 388, 389 on the respective interior, contacting portions of outer longitudinal members 382, 386 and interior longitudinal member 384.

FIG. 2T is a threaded pull rod fixation mechanism 390 similar in shape and form to pull rod fixation mechanism 230 shown in FIG. 2D. However, the respective interior contact points of longitudinal members 392, 396 and interior longitudinal member 394 have threaded portions 398, 399.

Figure 3A:
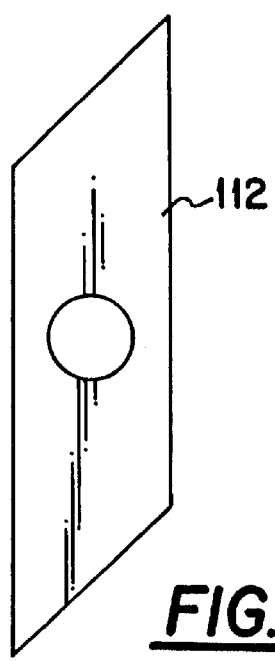
FIGS. 3A–3D are various views of the fixation mechanism shown in FIG. 2A.
Figure 3B:
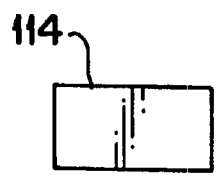
Figure 3C:
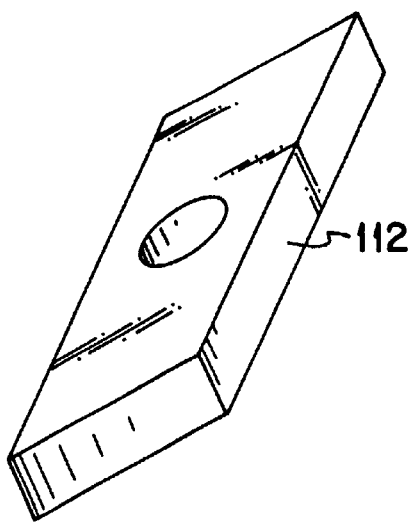
Figure 3D:
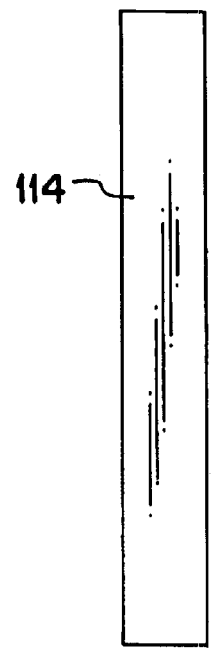

FIGS. 3A–3D show various views of the simple toggle fixation mechanism 110 shown in FIG. 2A. FIG. 3A is a side view of the parallelogram-shaped horizontal member 112 of the fixation mechanism. FIG. 3B is a top end view of the longitudinal member 114 of the fixation mechanism. FIG. 3C is a side elevated view of the parallelogram-shaped horizontal piece 112 of the fixation mechanism. FIG. 3D is a side view of the longitudinal member 114 of the fixation mechanism.

Figure 4A:
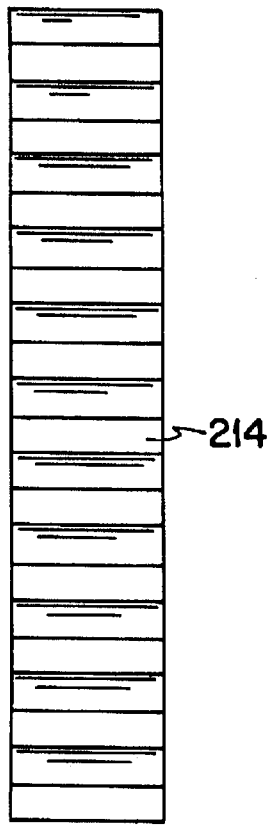
FIGS. 4A–4D are various views of the fixation mechanism shown in FIG. 2B.
Figure 4B:
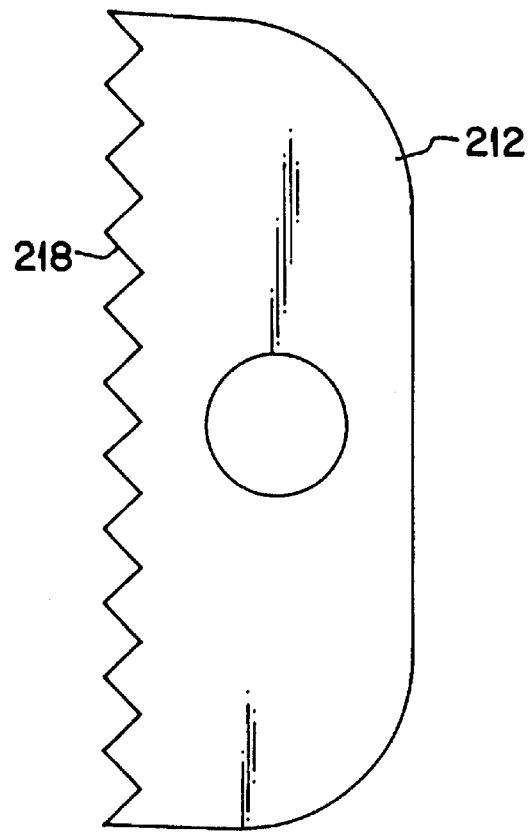
Figure 4C:
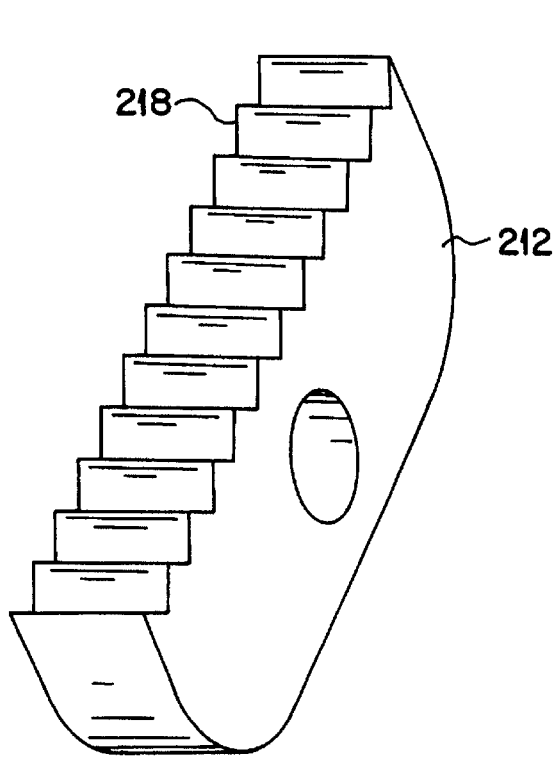
Figure 4D:
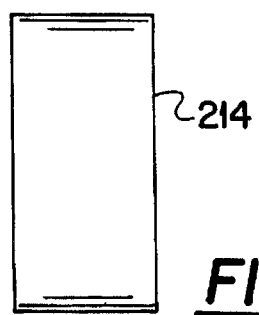

FIGS. 4A–4D show various views of the alternative simple toggle fixation mechanism 210 shown in FIG. 2B. FIG. 4A is a side view of the longitudinal member 214 of the fixation mechanism. FIG. 4B is a side view of the horizontal member 212 of the fixation mechanism. FIG. 4C is an elevated side view of the horizontal member 212 of the fixation mechanism with the teeth 218 exposed. FIG. 4D is a top end view of the longitudinal member 214 of the fixation mechanism.

Figure 5:
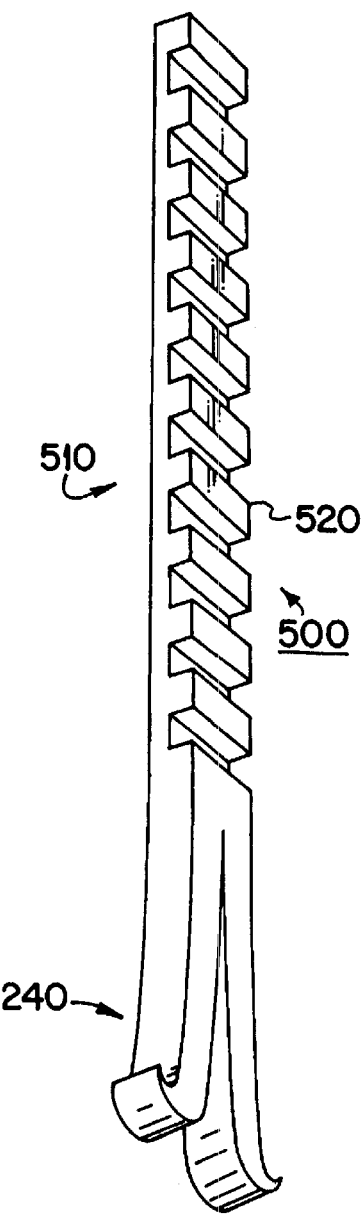
FIG. 5 depicts the fixation mechanism shown in FIG. 2E disposed on a shaft.

FIG. 5 depicts the fixation mechanism 240 shown in FIG. 2E disposed on a shaft 510. The shaft 510 has a plurality of raised portions 520 disposed thereon. Referring back to FIG. 1, the shaft 510 is disposed within the insertion tunnel such that the fixation mechanism disposed thereon (in FIG. 1, fixation mechanism 110) protrudes from an end of the insertion tunnel. The shaft 510, for instance, is a one-way track, which has, for example, pins, transverse tracks or bumps, intended to prevent a closely fit external sliding member, such as a securing mechanism, from reversing direction once it has started sliding on the shaft 510.

Figure 6A:
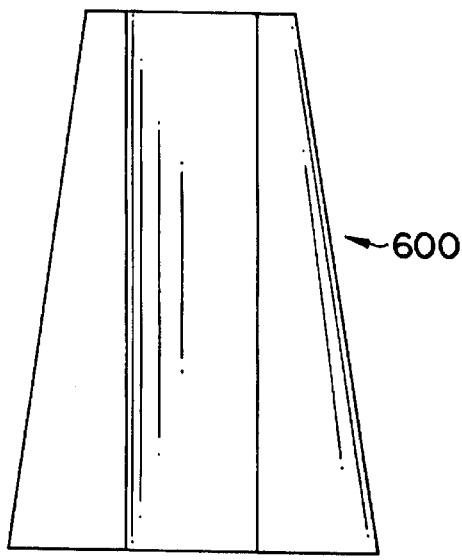
FIGS. 6A–6D are various views of a securing mechanism.
Figure 6B:
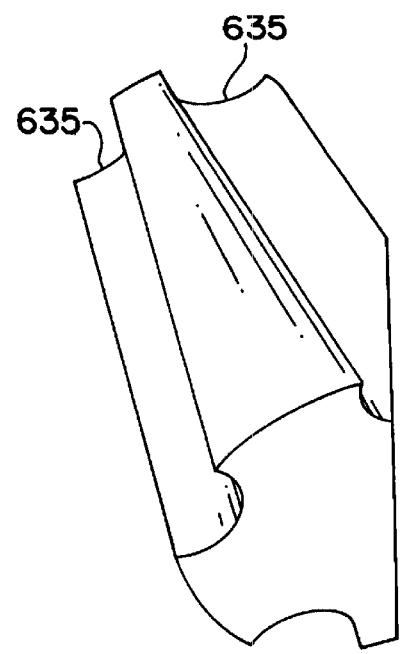
Figure 6C:
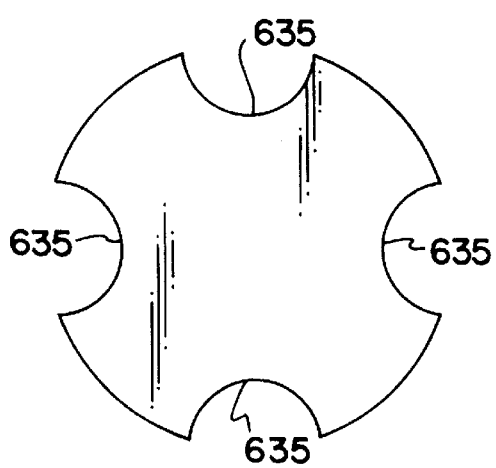
Figure 6D:
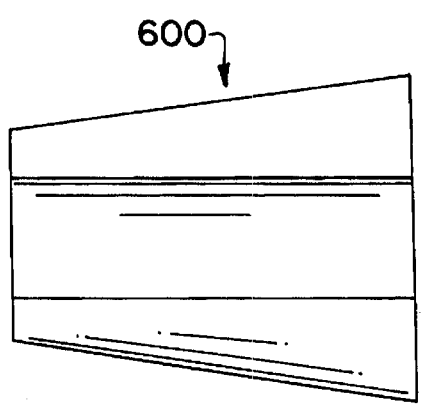

FIGS. 6A–6D show various views of a securing mechanism 600. Generally, a securing mechanism 600 has the shape of a plug with cutouts or channels 635, designed to support tendon grafts without damage, about its circumference, i.e., a support plug. FIG. 6A is a longitudinal side view of the securing mechanism 600. FIG. 6B is a schematic elevated perspective view of the securing mechanism 600 showing the cutouts 635 in the outer circumference of the securing mechanism 600. FIG. 6C is a schematic end view of the securing mechanism 600, showing the cutouts 635. FIG. 6D is a horizontal side view of the securing mechanism 600. The securing mechanism could be, for example, a cylindrical, a conical, a cubic, or a complex shape, which provides adequate radial force against the graft into the surrounding bone. The securing mechanism may be made of any biocompatible metal, polymer, bioabsorbable polymer, or bone. If bone is used, an additional securing mechanism must be used to provide the one-way locking on the shaft. The securing mechanism can transport site-specific drugs, such as bone morphing proteins, antibiotics, anti-inflammatories, and anesthetics.

Figure 7:
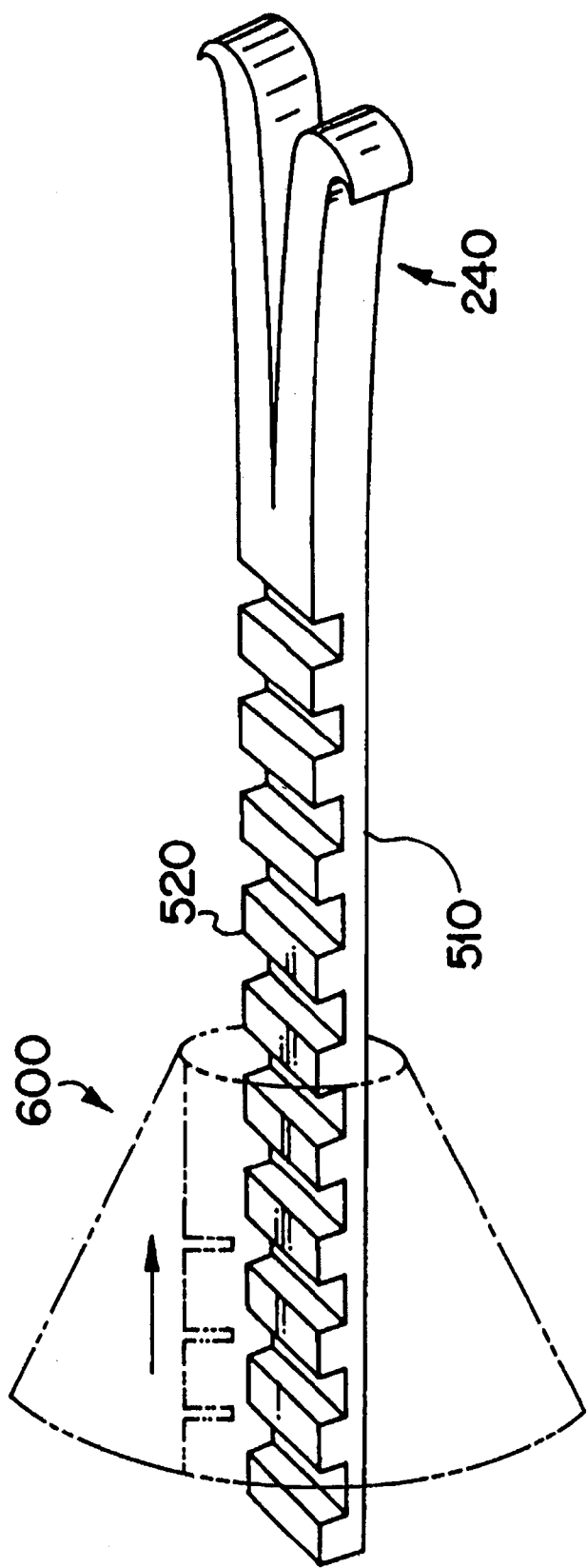
FIG. 7 schematically depicts the shaft and the securing mechanism disposed together.

FIG. 7 schematically depicts a fixation mechanism 240 on the shaft 510 and the securing mechanism 600 disposed together. The securing mechanism 600 is moved in the direction of the arrow along the shaft 510, whereby the securing mechanism 600 engages with the shaft 510 to lock in place.

The system of instrumentation and devices for attaching soft tissue to bone reduces the operating room time required to perform a procedure. The fixation device can be used in confined spaces, such as those in and around the human knee. The fixation device for attaching soft tissue to bone can be made of bioabsorbable, biopolymer, or biometal and can be easily removed and replaced. The devices can be deployed with one hand and allow the surgeon to individually tension each leg of an ACL graft. Using the system and/or device does not damage ACL grafts and a variety of graft sizes can be accommodated. Both ends of an ACL graft can be inserted through a single incision. Once the graft is in place, the securing mechanism radially presses the graft against the side of the insertion tunnel, maintaining maximum graft to bone area required for optimal healing. There is high resistance to pull out as compared to standard interference screws that are approximately 800 N on the femoral side.

The system of instrumentation and devices for surgically securing an allograft or prosthetic ligament in a patient's bone are used in a procedure to replace a patient's cruciate ligaments. As part of the replacement procedure for the anterior cruciate ligament, the patient's leg is bent at an approximately ninety (90°) degree angle and a single incision is made medial to the tibial tuberosity. Through this incision, an insertion tunnel is created at the desired insertion point of the graft using standard orthopaedic techniques. The insertion tunnel exits on the lateral aspect of the femoral cortex. A replacement ligament is prepared using a hamstring allograft.

The fixation device is loaded with the graft at full-length extension. The fixation mechanism is pushed into the insertion tunnel until it exits the femoral insertion tunnel. The fixation device is pulled back to allow the fixation mechanism to rotate to prevent further retrograde movement, i.e., in FIG. 1, the horizontal portion of the fixation mechanism 110, e.g., the toggle, rotates to a horizontal position across the femoral insertion tunnel. The shaft holds the fixation mechanism taut and the securing mechanism is slid forward into the insertion tunnel. Inside the securing mechanism is a one-way locking gate, which prevents retrograde movement of the securing mechanism along the shaft. The securing mechanism also presses the graft against the sidewall of the tunnel to facilitate healing over a larger area. The securing mechanism provides radial force to press the graft against the sidewall of the bone tunnel for faster and more efficient healing.

The graft is held in place within the femoral insertion tunnel by compression of the securing mechanism against the graft and is prevented from being pulled out of the insertion tunnel by the fixation mechanism. Once the femoral side of the graft is pressed in place and locked on the shaft, the tibial end of the graft is pulled into position and also locked into place.

An insertion instrument allows the surgeon to deploy the fixation device with one hand: position the fixation mechanism, push the securing mechanism, and cut off the excess length of the graft using one hand.

A number of implementations have been described. Nevertheless, it will be understood that various modifications may be made without departing from the spirit and scope. Accordingly, other implementations are within the scope of the following claims.

We claim:

1. A device for attaching soft tissue to bone comprising:
   a toggle pin member;
   an adjustable length track member; and
   a support plug which slides along the adjustable length track member.

2. The device of claim 1 wherein said support plug comprises an internal one-way locking mechanism.

3. A device for attaching soft tissue to bone comprising:
   an adjustable length strip member;
   a toggle element attached to the adjustable length strip member;
   a one-way track for inserting the adjustable length strip member therein and the toggle element therethrough; and
   a plug member for holding a graft within the one-way track by compressing the plug member against the graft.

4. The device of claim 3 wherein said plug member comprises at least one of a conical shape, a cylindrical shape, a cubic shape, or a complex shape capable of exerting an adequate radial force against the graft and into a surrounding bone.

* * * * *

UNITED STATES PATENT AND TRADEMARK OFFICE
CERTIFICATE OF CORRECTION

PATENT NO. : 6,482,210 B1
DATED : November 19, 2002
INVENTOR(S) : Jeffry B. Skiba and Jeffrey P. Baldwin It is certified that error appears in the above-identified patent and that said Letters Patent is hereby corrected as shown below:

<u>Column 4,</u>
Line 3, replace "FIG. 20" with -- FIG. 2O --

Signed and Sealed this

Twenty-sixth Day of August, 2003

JAMES E. ROGAN
*Director of the United States Patent and Trademark Office*